United States Patent [19]

Siclari et al.

[11] 4,164,508
[45] Aug. 14, 1979

[54] FORMYL ALKENOIC ACIDS

[75] Inventors: Francesco Siclari, Barlassina Milan; Pietro P. Rossi, Garlasco Pavia, both of Italy

[73] Assignee: Snia Viscosa Societa' Nazionale Industria Viscosa S.p.A., Italy

[21] Appl. No.: 885,475

[22] Filed: Mar. 13, 1978

Related U.S. Application Data

[62] Division of Ser. No. 486,992, Jul. 10, 1974, Pat. No. 4,085,127.

[30] Foreign Application Priority Data

Jul. 11, 1973 [IT] Italy ............................... 26479 A/73

[51] Int. Cl.$^2$ ............................................. C11C 1/00
[52] U.S. Cl. .................................... 260/413; 260/339
[58] Field of Search ........ 260/413 R, 413 Q, 413 HC, 260/413 K, 406

[56] References Cited

U.S. PATENT DOCUMENTS 3,856,833   12/1974   Siclari et al. ........................ 260/413

OTHER PUBLICATIONS

Crundwell, et al., Chem. Absts., vol. 75, 76095d, (1971).
Vig, et al., Chem. Absts., vol. 73, 159897e, (1973).
Mercier, et al., Chem. Absts., vol. 81, 109117u, (1974).
Morrison and Boyd, Organic Chemistry, 3rd ed., p. 675, (1973).

*Primary Examiner*—John Niebling
*Attorney, Agent, or Firm*—Shlesinger, Fitzsimmons & Shlesinger

[57] ABSTRACT

An omega formyl alkenoic acid containing from 8 to 12 carbon atoms is obtained by reacting a polyunsaturated hydrocarbon cycloolefin containing from 8 to 12 carbon atoms with ozone to form a mono-ozonide, which is then subjected to a transposition step to produce the omega formyl alkenoic acid.

2 Claims, 4 Drawing Figures

OHC-CH$_2$-CH$_2$-CH=CH-CH$_2$-CH$_2$-COOH   T.Q. (NaCl)

FORMYL ALKENOIC ACIDS

This is a division of our copending U.S. application Ser. No. 486,992, filed July 10, 1974, now U.S. Pat. No. 4,085,127.

This invention relates to omega-formyl alkenoic acids. Methods of producing omega formyl alkenoic acids starting from polyunsaturated cyclo-olefins are described in our above-noted copending U.S. patent application, the contents of which may be referred to if necessary better to understand the hereinafter described invention.

The acids claimed herein, and in particular certain of their unsaturated derivatives, have important applications e.g. use in making polymers or copolymers whose reactivity, due to the presence of double bonds, enables them to be used for the manufacture of products which in turn possess desirable properties. Examples of such products are textile products possessing a high degree of dyeability and additives for antistatic agents or for resins, all of which is easily understandable by persons skilled in the art.

As is known, cyclododecatriene-1,5,9, and likewise cyclodecadiene and cyclooctadiene, are products that are obtained by known processes of cyclization of butadiene, are currently available on the market and are supplied by refineries and industries which treat and process petroliferous products. These cyclooefins are in general transformed by the petroleum processing industries themselves, or by the utilizer industry, into the corresponding cyclomonounsaturated product. For example, cyclododecene is obtained, which is for example utilized for the production of conventional nylon 12.

The industrial utilization of starting materials which contain more than one unsaturation in order to obtain, with high conversions, acidic aldehydes and other open-chain unsaturated functional products is not known in the technical and patent literature of the art. Thus, at least within the limits of the applicant's knowledge, it can be held that no such technology existed previous to the present invention.

It is in fact known that the mono-ozonization of polyunsaturated olefins is a difficult operation, and that in practice it is performed only in the experimental field, with the obtaining of unacceptably low yields.

Generally, when an olefin has several double bonds, the ozonization is not selective and more than one double bond becomes ozonized.

In the ozonoization of cyclooctotetraene, i.e. of a cycloolefin having conjugated double bonds, for example (N. A. Milas—J. Org. Chem. 23 (1958/624), followed by reduction with sodium disulphite, there is obtained approximately 2.2 millimoles of glyoxal (OHC—CHO) per millimole of cyclooctotetraene, which is a result that indicates that more than one double bond has reacted with the ozone.

By ozonizing chlorinated cycloolefins in solution, either with polar solvents or with non-polar solvents or with mixtures of polar and non-polar solvents the ozonization of more than one double bond is avoided when the double bonds are not equivalent or are sterically impeded or non-reactive with ozone (J. E. Franz. U.S. Pat. No. 3,481,954).

In some cases it proves possible to ozonize only one double bond of a polyunsaturated cycloolefin by using a large excess of cycloolefin and a small amount of ozone. In such cases, the process is clearly uneconomic since it is necessary to separate, with complicated means, small amounts of mono-ozonide from large amounts of cycloolefin.

In the previously published French patent applications No. 72,05593 and No. 72,05594 (corresponding to applicants' U.S. Pat. No. 3,856,833 and 3,868,392) there was fully described and exemplified a particular method for the continuous production of the ozonide of a cycloolefin without superoxidation. The method is based on the principle of immediate separation of the hydroperoxide, which forms as the result of reaction of the oxonide with a reactive solvent, from the environment of ozonization, by means of the use of a non-solvent for the hydroperoxide.

The applicants have now found that a similar method may be applied, in the case of polyunsaturated hydrocarbon cycloolefins and that there is obtained a more rapid and instantaneous separation of the peroxide derivative of the ozonide if the concentration of the cycloolefin in the reaction mixture is kept between 10 and 40% by weight and if an anhydride of a carboxylic acid is added to the polar solvent, which comprises at least one carboxylic acid. The polar solvent, the anhydride of the carboxylic acid, the non-polar solvent and the polyunsaturated olefin must be at least partially soluble one with another.

The ozonide of a polyunsaturated cycloolefin is an important intermediate for the preparation of unsaturated polyfunctional compounds. The conversion of the monoozonide may be effected with yields which exceed 90%, by means of rearrangement of the ozonide at low temperature.

The reaction is catalyzed by a mixture of the anhydride of a carboxylic acid and an alkali metal salt or an organic base salt of a carboxylic acid or an alkali metal alcoholate. The concentration of the cycloolefin in the reaction mixture, the low temperature and the catalytic system reported are essential for the purposes of obtaining from the ozonide of a cycloolefin a single derived product and not mixtures of products.

It is in fact known (U.S. Pat. No. 2,891,988 in the name of Brokmann) that by heating the ozonides, even in the presence of reducing agents and of water, there are obtained more or less complexed mixtures of different compounds which are difficult to separate.

The present invention provides an alternative use of polyunsaturated cycloolefins, which previously, after production by cyclisation of butadiene have been subjected to selective or controlled hydrogenation to obtain their conversion into monounsaturated cycloolefins.

In fact such reduction gives rise to secondary products, for example in the case of cyclododecatriene, in addition to cyclododecene (even though in prevalent quantity) there are also formed cyclododecane and cyclododecadiene. The said secondary products are among other things a cause of low industrial efficiency, in that they correspond to amounts of starting material which cannot be converted into the end products. The separation of these secondary fractions is generally intricate, costly, and sometimes incomplete. Moreover, it is known that these initial methods of conversion of the starting polyunsaturated cycloolefin, and that is to say the processes of selective hydrogenation, are extremely expensive. This initial selective hydrogenation, which is considered indispensable according to the conventional methods should in particular be compared with the method characteristic of this invention, in which the polyunsaturated cycloolefins are converted by the conversion into the omegaformyl alkenoic acid.

The present invention provides an omega-formyl alkenoic acid containing from 8 to 12 carbon atoms.

The method of preparing this acid comprises reacting a polyunsaturated hydrocarbon cycloolefin containing from 8 to 12 carbon atoms with ozone to form a mono-ozonide, the reaction being carried out in a solvent system comprising a non-polar solvent and a polar solvent said polar solvent comprising at least one carboxylic acid and at least one anhydride of a carboxylic acid in a weight ratio of from 1:2 to 2:1, the concentration of said polyunsaturated cycloolefin in the reaction mixture being from 10 to 40% by weight, to form a solution of the mono-ozonide in the polar solvent, which solution is a separable phase, separating said phase and subjecting to transposition at a low temperature the monoozonide in the presence of a catalyst comprising a carboxylic acid anhydride in admixture with an alkali metal salt or an organic base salt of a carboxylic acid or an alkali metal alcoholate.

The non-polar solvent is preferably a saturated hydrocarbon, or a mixture of saturated hydrocarbons, e.g. cyclohexane, or paraffin oil or a mixture thereof.

The reaction mixture may suitably comprise 10 to 40% by weight of polyunsaturated cycloolefin, 55 to 85% by weight of a saturated aliphatic hydrocarbon, and 5 to 10% by weight of a mixture of acetic acid and acetic anhydride.

The ozone used in the reaction is preferably free of oxides of nitrogen which may be removed by passage of the ozone through a 1 to 10% by weight solution of sodium or potassium acetate in acetic acid, or by passage over copper oxide chips.

The catalyst for the transposition of the mono-ozonide may comprise sodium, potassium or pyridine acetate and acetic anhydride, e.g. from 1 to 7 moles of acetic anhydride from 1 to 7 moles of acetic acid and from 0.025 to 0.1 moles of sodium potassium or pyridine acetate per mole of mono-ozonide.

The omega-formyl alkenoic acids of the invention are unsaturated linear acids containing from 8 to 12 carbon atoms. When obtained from cyclododecatriene, they correspond to the formula:

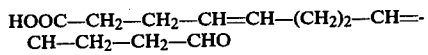

Clearly, the compounds that are obtained from the polyunsaturated cycloolefins having 8 to 10 carbon atoms correspond to similar formulae, but the rest attached to the acid group has 7 and 9 carbon atoms, respectively.

More particularly, according to the invention, the starting polyunsaturated cycloolefin, e.g. cyclododecatriene, cyclodecadiene or cyclooctadiene (independently, as has been said, of the form or mixture of isomeric forms and also, in the specific case of cyclododecatriene, possibly in admixture with cyclododecadiene) is treated by means of a sequence of steps and operations during which not more than one unsaturation is removed, the said sequence comprising a selective ozonization from which is obtained the mono-ozonide which is then converted by transposition into the omega-formyl-alkenoic acid, in the case in point 11-formyl-4,8-undecadienoic acid (as well as 11-formyl-4-undecenoic acid or 11-formyl-8-undecenoic acid and their mixtures), 7-formyl-4-heptenoic acid, 9-formyl-4-nonenoic acid and 9-formyl-6-nonenoic acid. From these acids a series of novel unsaturated products are readily obtainable, some of which are concrete and immediate industrial applicability.

In the course of the detailed description that follows, referred to various examples of execution of the invention, certain of these products and their possible uses are indicated.

For example, from 11-formyl undecadienoic acid there may be obtained 12-aminododecadienoic acid and thus 12-aminododecanoic acid, utilizable for the production of nylon 12. Similarly, from 7-formyl-heptenoic acid and 9-formyl nonenoic acid there may be obtained 8-aminooctenoic acid and 10-aminodecenoic acid respectively and from these 8-aminooctanoic acid and 10-aminodecanoic acid respectively which are utilizable for the production of nylon 8 and nylon 10 respectively.

The omega formyl alkenoic acids of the invention may also be subjected to a hydrogenation process (for instance with Pd+H$_2$) in order to yield the corresponding omega formyl alkanoic acid.

From among the other novel unsaturated products that can be obtained from the omega-formyl alkenoic acids of the invention, there can be mentioned 12-hydroxy-4,8-dodecadienoic acid and 8-hydroxy-4-octenoic acid, from which there can be obtained unsaturated esters particularly methyl esters and/or polyesters, as well as a series of by-products, among which 1,12-diaminododecadiene (-4,8-) has been identified.

Over and above these, the 1,12-dodeca-4,8-dienediamine and 1,12-dodecandioic acid are derivable from the appropriate omega-formyl acid. From these, by polycondensation, there is obtained unsaturated 12,12 nylon, or, by hydrogenation of the olefinic unsaturations and subsequent polycondensation, -saturated 12,12 nylon.

This method has proved possible as a result of the fact that out of the plurality of double bonds present in the starting polyunsaturated cycloolefin, in particular out of the two or three double bonds available, only one is eliminated in the said sequence of steps and operations (provided suitable expedients are adopted), which is not suggested by the prior art. This preservation of double bonds is the essential factor enabling the aforesaid products to be obtained and, forseeably, also numerous other unsaturated products and derivatives. The fact that such sequence of steps generally comprises ozonization of cycloolefins and subsequent treatments directed towards the obtaining of acidic aldehydes (in the field of saturated products) does not alter the novelty or importance of the method according to the invention. These known methods and treatments have been only recently and to a limited extent divulged. As regards the production of these saturated acidic aldehydes by means of ozonization of the corresponding cycloolefin, reference is made to our two above-noted U.S. Pat. Nos. 3,856,833 and 3,868,392.

To further describe the present invention, there is hereafter set out a detailed exemplification of methods of obtaining the novel products according to the invention. The disclosure is completed by the annexed drawings, in which:

FIG. 3 shows the IR spectrum of 11-formyl-t,t-4,8-undecadienoic acid;

FIG. 4 shows the IR spectrum of 7-formyl-cis-4-heptenoic acid.

Figure 3:
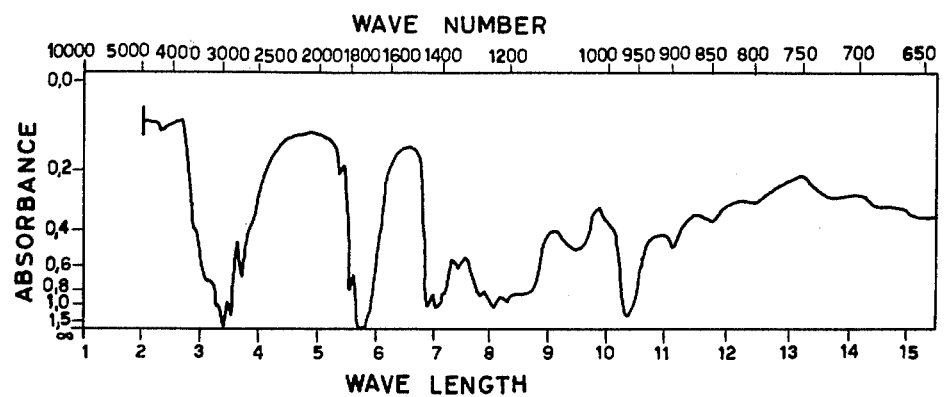
FIGS. 3 and 4 show a number of IR spectra in respect of certain unsaturated compounds obtainable according to the invention, in particular.

Examination of these spectra clearly reveals the following: for the spectrum represented by FIG. 3 the band of the trans double bond (960 cm$^-$) is preserved.

Figure 4:
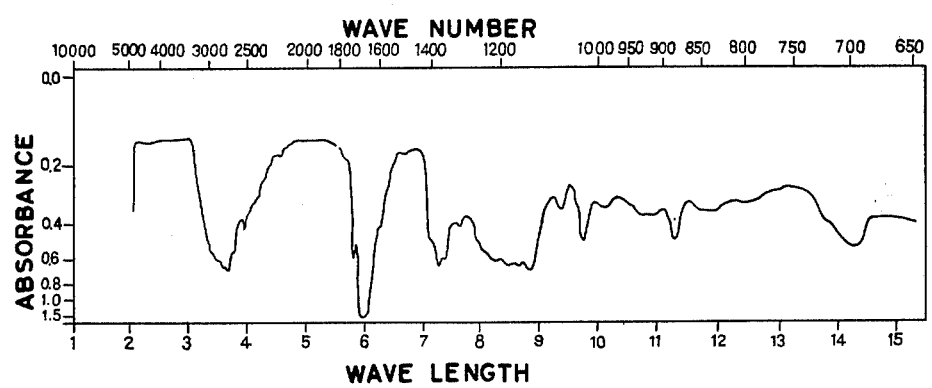

FIG. 4 represents the 8-unsaturated acidic aldehyde obtained from the cis,cis-1,5-cyclooctadiene, the cis band between 680 and 740 cm$^{-1}$ is preserved, while there are clearly visible the bands characteristic of the aldehyde group.

In the ensuing description specific indication will be given of the stereoisomeric forms and their proportions in the mixtures utilized, in the interests of greater bearing on the industrial field, in view of the availability on the market of polyunsaturated cycloolefins, c.g. cyclododecatriene, cyclodecadiene and cyclooctadiene in various stereoisomeric forms.

In the IR spectra shown in FIG. 3, on the other hand, 1,5,9-t,t,t-cycloodecatriene has been specified as starting material simply because the derivatives show clearly in the IR the trans isomerism of the double bond, without this in any way limiting the scope of the invention, while for the cyclooctadiene the material used was cis-cis-1,5-cyclooctadiene.

The method characteristic of the invention will be described hereinafter summarily in its industrial applications directed towards providing a starting material for the manufacture of 12-aminododecanoic acid, in its turn destined for the production of nylon 12, (which, although selected as example, is not restrictive of the invention. The technology in question is applicable to e.g. nylons 8 and 10).

Clearly, the unsaturated omega-formyl alkenoic acids of the invention are in such cases merely intermediates for this complete process.

Figure 1:
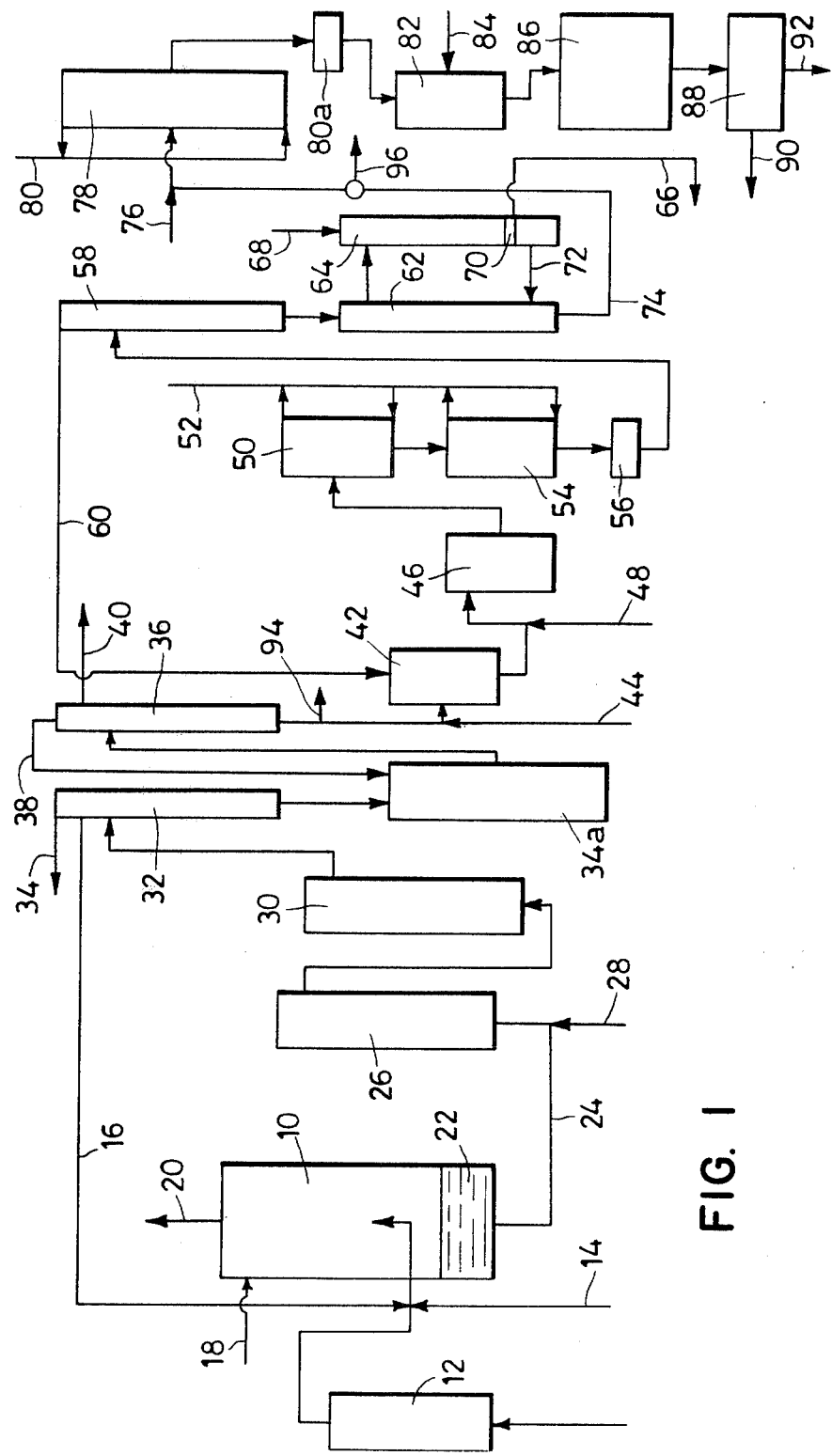
FIG. 1 shows schematically, in that the various components are individually well known, an installation utilizable for the preparation of 12-formyl dodecadienoic acid from cyclododecatriene.

An apparatus for carrying out the method of the invention is schematically represented in FIG. 1.

The initial step of treatment of the polyunsaturated cycloolefin with ozone is carried out in the vessel or reaction environment indicated generally by 10, in association with an apparatus 12 for production of ozone, after prior preparation of a stationary phase consisting of a mixture of high-boiling saturated hydrocarbon, preferably obtained from mineral oil (Vaseline (Vaseline is a Registered Trade Mark) oil or refinery cuttings) with a polar solvent, such as acetic acid, and acetic anhydride. The ozone is used in the form of a mixture of $O_2 + O_3$ containing from 5 to 80 grams, and preferably from 15 to 60 grams of $O_3$ per cubic meter, or a mixture of $O_2 + O_3 + CO_2$ containing from 5 to 50 grams of ozone per cubic meter. Alternatively the ozone may be mixed with purified air, stripped of nitrogen oxides by passing through sodium acetate dissolved in acetic acid or by passing over CuO. The mixtures may contain from 1 to 50 grams of $O_3$ per cubic meter. The ozonide is continuously deposited in the container bottom as it is formed as a heavy phase P formed by solution in the acetic acid and acetic anhydride. This stage may be carried out at any temperature between 5° C. and 45° C. The acetic acid and acetic anhydride is fed into the apparatus at 14 and also recycled at 16. Cyclododecatriene is fed into the vessel 10 continuously at 18, while at 20 the oxygen or other gas used as a vehicle for ozone is discharged.

The heavy phase 22 is metered and sent at 24 into a transposition apparatus 26 into which there is also metered at 28 an additional transposition catalyst, preferably sodium acetate, and possibly potassium acetate, sodium propionate or potassium propionate. Acetic acid is present in the solution from the first stage.

The transposition stage which is the decomposition of the ozonide in the vessel 26 may be carried out at a temperature of from 10° to 50° C., a solution of the unsaturated acidic aldehyde in acetic acid and/or acetic anhydride being obtained. Preferably, the transposition run is carried out progressively in a set of vessels and in the embodiment of FIG. 1 this is achieved by transforming the solution to a second apparatus 30 from which the product is passed to an evaporator 32. From the evaporator the excess acetic acid is removed at 34, and the remaining acetic acid and/or acetic anhydride which is distilled off is recycled at 16 into the ozonization vessel or environment 10. The temperature in the two transposition stages (26-30) can either be the same or it can be different. Usually it is higher in vessel 30.

The anhydride of the acidic aldehyde left in the evaporator 32, is transferred to a hydrolysis apparatus 34a. The hydrolysis of the acidic aldehyde anhydride is carried out in this apparatus. Hydrolysis may be effected with water at a temperature of from 50° C. to 100° C. The solution is transferred to an evaporator 36, wherefrom the hydrolysis water is recycled at 38 into the hydrolysis apparatus 34a. A mixture of the excess water and possibly acetic acid is dumped, at 40. The acidic aldehyde is discharged from the bottom of the evaporator 36.

Figure 2:
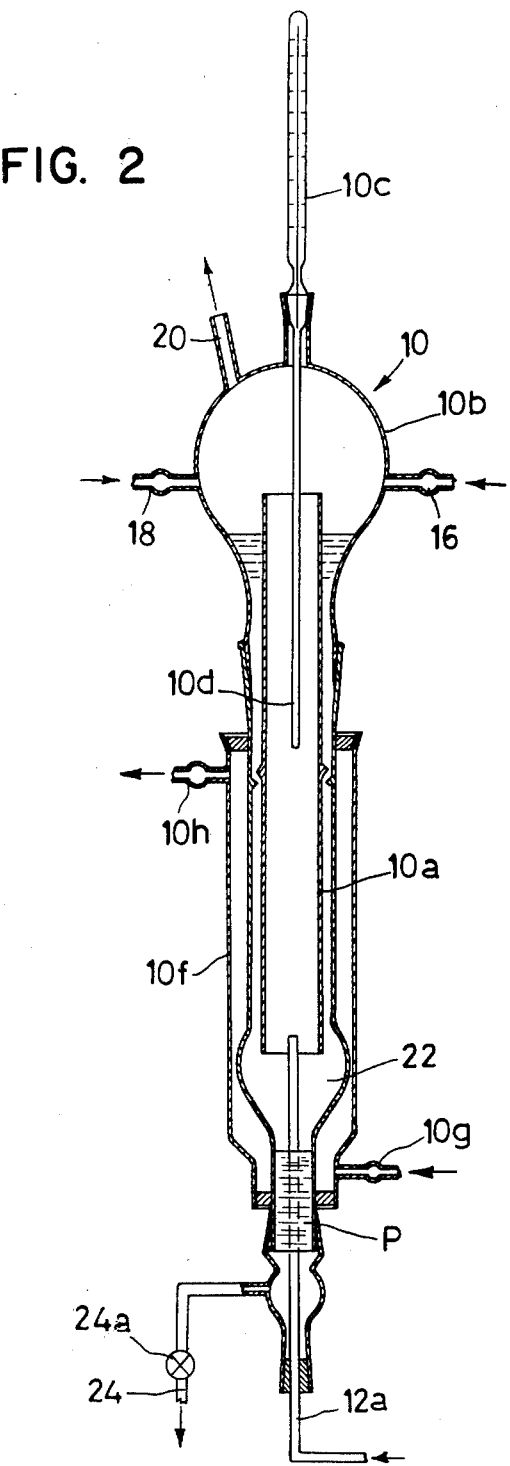
FIG. 2 shows in greater detail the equipment preferably used for the ozonization step.

A preferred embodiment of the ozonization apparatus 10 is reproduced in detail, in FIG. 2 in which the same reference numerals connote the same parts as equivalent numbers in FIG. 1.

This apparatus comprises an internal reaction tube 10a, whose top end enters a flask 10b in which open the outlet 20 for the oxygen, and the ducts 18 for feeding in cyclododecatriene and 16 for feeding in the recycled acetic acid and/or anhydride. At 12a there is indicated the duct at the base of the reaction environment through which the product of the ozone ($O_2 + O_3$) producing apparatus 12 is introduced and at 24 there is indicated the discharge duct for the ozonide, equipped with a suitable valve 24a.

The apparatus is completed by an appropriate thermometer 10C whose sensitive bulb 10d is extended into the reaction tube. The portion in which reaction mainly occurs is cooled by an outer jacket 10f for an appropriate coolant mixture and having integral inlet and outlet fittings 10g and 10h.

There follow specific examples describing parameters and conditions which are deemed more suitable for carrying out the invention with high yields.

EXAMPLES

Group I (Ozonization)

I (1) Ozonization of t,t,t-1,5,9-cyclododecatriene (CDT) in acetic acid-acetic anhydride-paraffin oil In this example there is described the preparation of the CDT mono-ozonide by ozonization in a mixed solvent, formed from acetic acid, acetic anhydride, and paraffin oil.

In the vessel 10 of FIG. 1 there was charged 800 grams of t,t,t-1,5,9-cyclododecatriene (m.p.=30°-32° C.), (97.5% trans, trans, trans, isomer), 297 grams acetic acid, 503 grams acetic anhydride (purity 95.2%) and 6400 grams of paraffin oil. The temperature of the mixture was brought to 20° C. and 113.5 grams/hour of ozone in 1700 liters/hour of oxygen (at ambient pressures), 736 grams/hour of acetic anhydride, 585 grams/hour of acetic acid, 400 grams/hour of CDT and 80 grams/hour of paraffin oil were continuously fed into the vessel.

A heavy phase was continuously deposited on the bottom of the reactor vessel at the rate of 1900 grams/hour, which phase consisted of CDT mono-ozonide dissolved in the acetic anhydride-acetic acid mixture.

After 16 working hours, 30410 grams of ozonide solution had been continuously discharged from the bottom of the reactor and sent to the transposition apparatus (No. 26, FIG. 1). The content of active oxygen (from iodometric assay according to Lohaus) was 37 mols overall, corresponding to 7760 grams of CDT ozonide as expressed in its classical form, the remainder being acetic anhydride, acetic acid and small quantities of cyclododecatriene and paraffin oil.

The total reacted cyclododecatriene (calculated from the amount charged, from what is left in the reactor and what is contained in the heavy phase) was 37.5 mols, a result which, as a rough estimate, indicates that CDT has reacted with ozone in a ratio of 1:1.

These data show that it is possible quantitatively to convert a polyunsaturated cycloolefin into its mono-ozonide. By employing paraffin oil, hydrocarbon losses in the reaction gas are prevented.

I (2) Ozonization of t,t,t-CDT in acetic acid-acetic anhydride-cyclohexane

In this example, the paraffin oil of Example I (1) was replaced by cyclohexane.

The Example I (1) was repeated employing cyclohexane in lieu of paraffin oil, and, in this case, too, a 1:1 reaction of CDT in ozone was obtained, although some cyclohexane was removed by the reaction gas and it was thus necessary to re-add it in the ozonizer.

I (3) Ozonization of cis,cis-1,5-cyclooctadiene

The Example I (2) was repeated, using cyclooctadiene (COD) as the polyunsaturated cycloolefin.

From the relative quantities of cycloolefin and ozone reacted it was seen that, in this case also, the ozone reacted in 1:1 molar ratio with the COD. The ozonide of the COD is a product useful for obtaining unsaturated aldehyde acids, bicarboxylic acids, etc.

I (4) Ozonization of cis,trans-1,5-cyclodecadiene

The example No. I (2) was repeated (using cyclodecadiene (CDD) as cycloolefin). In this case as well, a 1:1 reaction between olefin and ozone was found.

The ozonide of CDD is an important product in that, besides having uses analogous to those recalled in respect of the ozonides of CDT and COD, it can serve as intermediate for the preparation of sebacic acid which plays a part in the field of plastics, additives, finishings for synthetic fibres.

I (5) Ozonization of t,t,t-CDT in acetic acid-acetic anhydride cyclohexane by employing a mixture of oxygen, ozone and carbon dioxide.

For the ozonization reaction pure ozone-laden oxygen can be used, or, on account of the hazards due to pure oxygen, there can be used a mixture of oxygen, carbon dioxide and ozone, in which the ratio of the three components of the gas mixture can be varied within a wide range. It is also possible to use air or ozone; in the latter case, however, the mixture of air and ozone contains nitrogen oxides which as nitrogenous acids tend to cause the polymerization of the ozonide as formed in the ozonization and thus do not permit to use this mixture in the industrial ozonizations. The Applicants have found that by passing ozone-laden air on chips of copper oxide or through a solution of sodium acetate in glacial acetic acid, a gaseous mixture is obtained which is deprived of those nitrogen oxides which could originate nitrogenous acids.

Example I (2) was repeated by employing as the ozonizing gas, instead of the mixture ozone and oxygen, a mixture of ozone-oxygen-carbon dioxide formed by 2.5% ozone, 57.5% oxygen and 40% of carbon dioxide, by volume. In this case also the CDT mono-ozonide was obtained with a yield of 95%.

I (6) Ozonization of cis,t,t-CDT; cis,cis,t-CDT and t,t,t-CDT in acetic acid, acetic anhydride paraffin oil The Example I (1) was repeated, using a mixture of the various stereoisomers of CDT (70% of cis,t,t-CDT; 27% of t,t,t-CDT; 2% of cis,cis,t-CDT and 1% of cyclododecane). The ozonizing gas consisted of a mixture of oxygen, ozone/carbon dioxide as in the Example I (5).

From the ozonization there was exclusively obtained the mono-ozonide of CDT.

I (7) Ozonization of t,t,t-CDT with air and ozone stripped from nitrogen oxides by copper oxide.

Example I (1) was repeated by employing a mixture of ozone-laden air which was previously passed over copper oxide chips. The ozonide obtained was not polymerized and was formed as in the Example I (1).

I (8) Ozonization of t,t,t-CDT with ozone-laden air stripped of the nitrogen oxides by passing it over an acetic acid solution of sodium acetate Example I (1) was repeated. The ozone-laden air was passed through a solution of 2% sodium acetate in glacial acetic acid. The gas emerged from the absorber virtually deprived of nitrogen oxides while the ozone content did not undergo any decrease. The cyclododecatriene was ozonized with this mixture and the results were equal to those of Example I (1).

I (9) Ozonization of cyclododecadiene

Cyclododecadiene was used as the polyunsaturated olefin, in repeating the ozonization as described at I (1). The ozonide as separated contained 95% of mono-ozonide of cyclododecadiene.

EXAMPLES

Group II (Transposition)

II (1) Transposition of the mono-ozonide of t,t,t-CDT into 11-formyl-t,t-4,8-undecadienoic acid The transposition of the CDT mono-ozonide into 11-formyl-t,t-4,8-undecadienoic acid may be carried out catalytically as described in the Examples that follow. The 11-formylundecanoic acid and the aldehyde acids and the analogous series (having 8 to 10 carbon atoms) are important intermediates for their conversion into amino-acids, hydroxyacids, esters, for example for resins, etc.

The ozonide solution (1900 grams/hour) coming from the apparatus 10 of FIG. 1, was sent continuously onto the bottom of a first transposition apparatus (26, FIG. 1) consisting of a 6-compartment steel cylinder fitted with thermometer, turbine type stirrer and temperature-regulation jacket kept at 20° C. The transposition apparatus was also continuously fed with 4.75 grams/hour of sodium acetate dissolved in 42.8 grams of acetic acid. The mixture issuing from the top of the first transposition apparatus passed to a second transposition apparatus (30, FIG. 1) which was the same as the first and was temperature-regulated at 30° C. Both the transposition apparatuses were kept under an inert gas atmosphere (carbon dioxide). The overall stay time was 7 hours and 30 minutes. Stirring was very slow.

Taking as equal to 100 the percentage of active oxygen (peroxide oxygen) at the inlet of the first transposition apparatus, the analysis of this latter variable at the outlet of the first transposition apparatus was 31.7% and at the outlet of the second transposition apparatus was 7.6% (conversion 92.4%). The solution coming out of the second transposition apparatus was sent to a liquid-film evaporator (32, FIG. 1) to remove the solvents. The residue, 426 grams/hour, of a liquid oily at room temperature, is continuously treated at 72° C. with 526 grams/hour of water (stay time 60 minutes) in an inert gas (nitrogen) atmosphere (34, FIG. 1). The water was again evaporated as a liquid film (36, FIG. 1). There was obtained 539 grams/hour of an oily residue which still contained small amounts of water, acetic acid and paraffin oil; it had the following characteristics:

| Aldehyde groups | 4.2 millimols/gram |
| Acidic groups | 4.5 millimols/gram |
| double bonds | 8.8 millimols/gram |

The product boiled at 180°–183° C. at 3 mm. of residual pressure, and consists of 11-formyl-t,t-4,8-undecadienoic acid.

II (2) Transposition of the ozonide of cyclooctadiene

The Example No. II (1) was repeated, using the product obtained in Example I (3), that is to say the mono-ozonide of cyclooctadiene (COD) was subjected to transposition.

There was obtained 7-formyl-4-heptenoic acid, which on analysis showed the following characteristics: b.p. at 2.3 mm.Hg = 146.5° C. $D^{20}$ = 1.4744

| | Calculated | Found |
|---|---|---|
| double bonds (mmols from $H_2$/g | 6.4 | 6.5 |
| -CHO- groups (titration with $H_2NOH \cdot HCl$) | 6.4 | 6.3 |
| -COOH groups (titration with NaOH) | 6.4 | 6.6 |

II (3) Transposition of the ozonide of cyclodecadiene

The Example No. II (1) was repeated, using the product obtained in the Example I (4), that is to say transposing the mono-ozonide of cyclodecadiene (CDD). There was obtained a mixture of the 9-formyl-nonenoic acids, that is to say of 9-formyl-4-nonenoic acid and 9-formyl-6-nonenoic acid.

II (4) Transposition of the CDT monoozonide obtained from the ozonization of mixtures of cis,t,t-CDT; cis,cis,-t-CDT and t,t,t-CDT to 11-formyl-4,8-undecadienoic acid The product as obtained in Example I (6) was subjected to transposition as described in Examples II (1). An oily compound was obtained at a rate of 528 grams/hour which was a mixture of the steric isomers of 11-formyl-4,8-undecadienoic acid.

The product had a boiling point of 178° C.–185° C. under 3 mms of mercury.

II (5) Transposition of the mono-ozonide of t,t,t-CDT in acetic anhydride-potassium acetate.

1900 grams/hour of a solution of the monoozonide of CDT (see Example I (1)) were continuously fed to the bottom of a first transposition apparatus together with 5.5 grams/hour of potassium acetate dissolved in 45 grams of glacial acetic acid. The temperature of the transposition was maintained at 25° C. while a temperature of 35° C. was maintained in the second transposition apparatus.

By adopting the procedure set forth in Example II (1) there was obtained 545 grams/hour of 11-formyl-t,t,4,8 undecadienoic acid, impure due to small amounts of CDT paraffin oil-acetic acid and water.

II (6) Transposition of the mono-ozonide of CDT in pyridine.

The procedure set forth in Example II (5) was adopted by using pyridine-acetic anhydride as the transposition agent. At 30° C. (first transposition apparatus) and at 45° C. (second transposition apparatus) a 96% conversion of the active oxygen was obtained.

II (7) Transposition of the mono oxonide of cyclododecadiene into 11-formyl-4-undecenoic acid and 11-formyl-8-undecenoic acid Example II (1) was repeated by effecting the transposition on the mono-ozonide of cyclododecadiene prepared according to Example I (9). There was obtained, in total, 515 grams/hour of 11-formyl-4-undecenoic acid and 11-formyl-8-undecenoic acid.

In the Examples there has been shown the advantageous production of unsaturated acidic aldehyde.

As specifically exemplified the present invention possesses the following advantages:

the starting unsaturated cycloolefins, such as cyclododecatriene and cyclooctadiene as available on the market, can be considered high-purity products. Even in the case of cyclododecatriene, which is in practice a mixture of its various stereoisomeric forms, the product cannot for such reason be considered impure, in view of the practically identical behavior of these stereoisomeric forms in the subsequent treatment and conversions (ascertained by the Applicants), even though they lead to physico-chemical diversities in the unsaturated end-products, which fact in its turn represents an advantage in that it makes possible the selective obtaining of unsaturated compounds having different properties.

In the case of production of unsaturated aminoacids, the said unsaturated end-products (in the case in point 12-amino-dodecadienoic-10-aminodecenoic and 8-amino-octenoic acids), when subjected to saturation processes, in particular hydrogenation, for the obtaining of the corresponding saturated aminoacids, always lead to saturated end-products having identical characteristics and properties, which are thus perfectly suitable for the subsequent processings or industrial productions foreseen.

EXAMPLES (Group III)

The preparation of the saturated acidic aldehyde from the unsaturated acidic aldehydes is described in the series of Examples from Group III.

III (1)—(Saturated acidic aldehyde from unsaturated acidic aldehyde at 20° C.).

Two hundred grams of 11-formyl-4,8-undecadienoic acid consisting of a mixture of the trans, trans and cis, trans isomers, having boiling range of 179°–182°. C. at 3 mm.Hg. (purity 90% - Analysis: Aldehyde groups=4.3 mmols/gram; acidic groups=4.4 mmols/gram - double bonds=8.6 mmols/gram, was dissolved in 466 grams of 98% acetic acid and charged into a steel autoclave, volume 1270 cu.cm. equipped with magnetic stirrer and with a temperature-regulation system made up of a jacket within which temperature-controlled water flows.

The autoclave was washed with nitrogen under nitrogen 8 grams of 5% Pd on carbon are charged. Then washing with hydrogen was carried out and 20 atmospheres of H$_2$ were charged.

The heat-regulation water was brought to 15° C. and circulated in the jacket of the autoclave. When the liquid inside the autoclave had reached a temperature of 15° C., stirring was commenced. The pressure dropped rapidly and, when it reached 10 Atm., hydrogen was again charged at 20 atmospheres.

The reaction temperature rose from 15° to 20° C. and remained steady at this value. Over a total period of 20 minutes 52 atmospheres of hydrogen were charged and, after this time, the absorption of hydrogen was practically complete.

The contents of the autoclave were decompressed, placed under nitrogen and the solution was discharged through a filter. The filtrate was evaporated to dryness under vacuum.

196 grams of a waxy white solid residue with m.p. 62–64C and consisting of 11-formyl-undecanoic acid was obtained. (Analysis—CHO Group=4.28 millimols—COOH Groups=4.5 millimols/gram - double bonds=traces).

III (2) - (Saturated acidic aldehyde from unsaturated acidic aldehyde at 40° C.).

Into the autoclave utilized in the Example III (1) there were charged 232 grams of 11-formyl-4,8-undecadienoic acid as used in Example No. III (1), dissolved in 542 grams of 90% acetic acid (the remainder consisting of water). The procedure was as in Example III (1) but the temperature-regulating water was at 35° C. Into the autoclave there were placed 10 grams of 5% Pd on carbon and the pressure was raised to 20 atmospheres of hydrogen. When the temperature inside the autoclave was at 32° C., stirring was started and, when the pressure fell to 10 atmospheres, it was brought back to 20 atmospheres. During the reaction the temperature—by effect of the heat of the reaction—rose to 40° C. After 36 minutes the absorption of hydrogen ceased. After a further five minutes the autoclave was decompressed, the catalyst was filtered and the acetic solution was evaporated under vacuum.

There was obtained 225 grams of 11-formyl-undecanoic acid, m.p. 61°–64° C.

III (3) - (7-formyl-heptanoic acid from 7-formyl-heptenoic acid).

86 grams of 7-formyl-4-heptenoic acid (characteristics; boiling point 146.5° C. at 2.3 mm hg $D^{20}$=1.4744; aldehyde groups=6.35 mmols/grams; acidic groups=6.6 mmols/gram; double bonds=6.52 mmols/gram) was dissolved in 300 grams of glacial acetic acid, and placed into the steel autoclave described in the Example III (1). The autoclave was washed with nitrogen, 2 grams of 5% Pd on carbon were charged and placed under a pressure of 15 atmospheres with hydrogen.

The temperature of the temperature-regulating liquid rose 15° C. and, when the internal temperature was 15° C., stirring was commenced, maintaining a constant pressure of 15 atmospheres.

After 20 minutes the absorption of hydrogen ceased. The solution was discharged, filtered from the catalyst and the solvent was evaporated under vacuum.

There was obtained 86.5 grams of 7-formyl-heptanoic acid with b.p.$_{0.1}$=130°–132° C.

By applying the procedure described to 9-formyl-4-nonenoic acid there was obtained the 9-formyl-4-nonanoic acid.

Having thus described our invention, what we claim is:

1. An omega-formyl alkenoic acid containing 8, 10 or 12 carbon atoms and selected from the group consisting of 11-formyl-4,8-undecadienoic acid, 11 formyl-4-undecenoic acid, 11-formul-8-undecenoic acid, 7-formyl-4-heptenoic acid, 9-formyl-4-nonenoic acid, 9-formyl-6-nonenoic acid, and mixtures thereof.

2. An omega-formyl alkenoic acid consisting of 11-formyl-undeca-4,8-dienoic acid, selectively in its stereoisomeric form having both the olefinic unsaturation of trans type, and in its stereoisomeric form having one of the olefinic unsaturations of the trans type and the other of cis type, and in the form of a mixture of acids of said stereoisomeric forms.

* * * * *